US00PP20168P2

(12) United States Plant Patent
Meilland

(10) Patent No.: US PP20,168 P2
(45) Date of Patent: Jul. 7, 2009

(54) FLORIBUNDA ROSE NAMED 'MEIZERBIL'

(50) Latin Name: *Rosa hybrida*
Varietal Denomination: Meizerbil

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/213,454

(22) Filed: Jun. 19, 2008

(51) Int. Cl.
*A01H 5/00* (2006.01)

(52) U.S. Cl. ..... Plt./141

(58) Field of Classification Search ..... Plt./141
See application file for complete search history.

*Primary Examiner*—Annette H Para
(74) *Attorney, Agent, or Firm*—Buchanan Ingersoll & Rooney PC

(57) ABSTRACT

A new and distinct Floribunda rose plant is provided which forms attractive red-purple blossoms having a yellow eye. The plant exhibits strong vegetation, a compact bushy growth habit, and dark green foliage with a semi-glossy aspect. The disease resistance is excellent particularly with respect to Oidium and Black Spot. The attractive dark green foliage contrasts nicely with the red-purple blossom coloration. The new variety is well suited for growing as attractive ornamentation in parks and gardens.

1 Drawing Sheet

Figures 1, 2, 3, 4, 5, 6, 7, 8, 9, 10, 11, 12, 13, 14, 15, 16, 17:
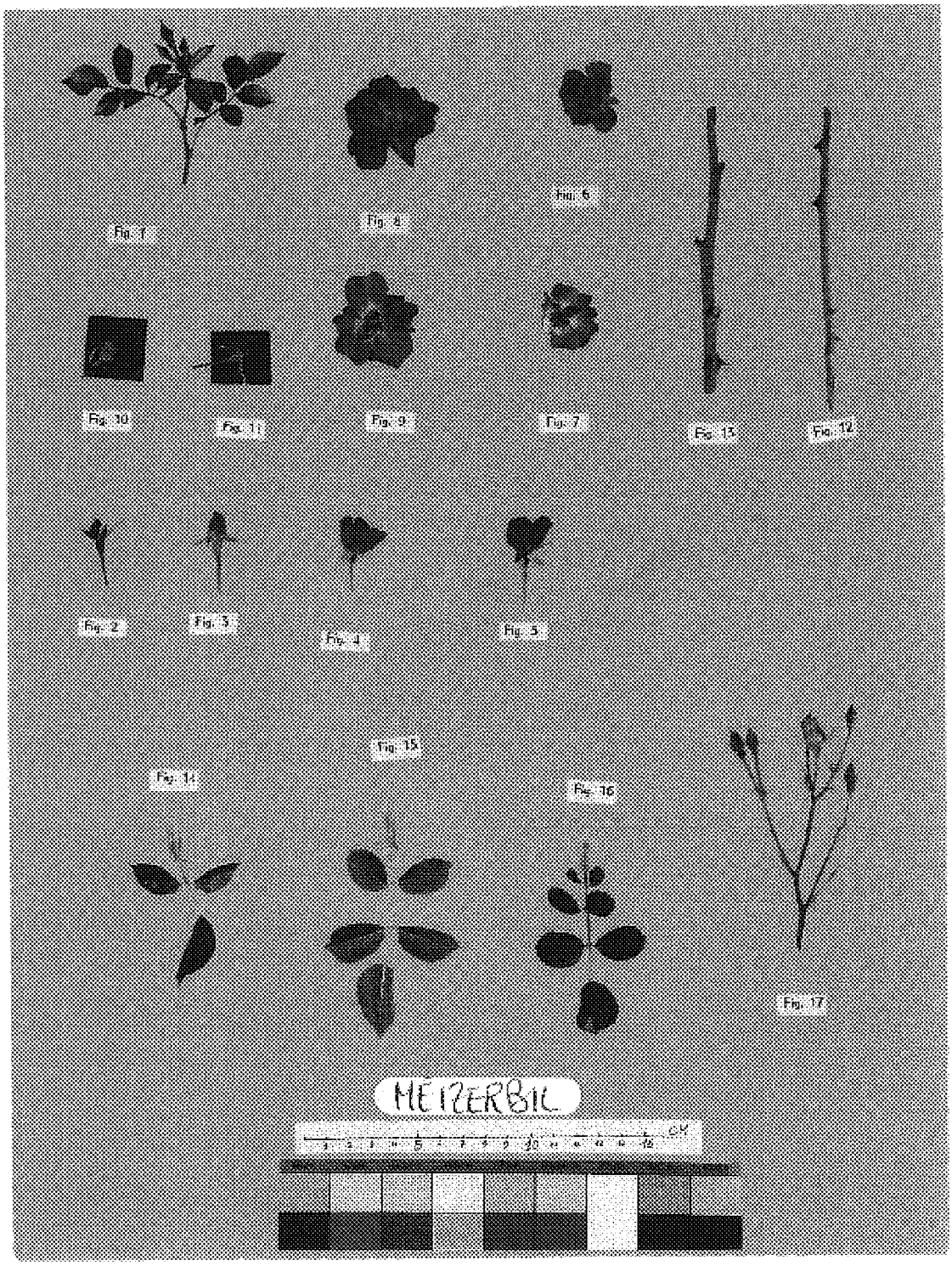

Botanical/commercial classification: *Rosa hybrida*/Floribunda Rose Plant.
Varietal denomination: cv. Meizerbil.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was 'The Fairy' variety (non-patented in the United States). The male parent (i.e., the pollen parent) was the product of the cross of the 'Meikrotal' variety (U.S. Plant Pat. No. 6,087) and the 'Kormax' variety (non-patented in the United States. The parentage of the new variety can be summarized as follows:

'The Fairy'×('Meikrotal'×'Kormax').

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a compact bushy growth habit, (b) forms attractive red-purple blossoms having a yellow eye, (c) forms attractive dark green semi-glossy foliage, (d) displays excellent resistance to disease, and (e) is well suited for growing as ornamentation in parks and gardens.

The disease resistance is particularly good with respect to Oidium and Black Spot. The dark green foliage coloration contrasts nicely with the red-purple blossom coloration.

The new variety well meets the needs of the horticultural industry and can be grown to advantage in the landscape where attractive ornamentation is desired.

The new variety can be readily distinguished from its ancestors. For instance, the 'The Fairy' variety displays light pink blossoms. The 'Meikrotal' variety displays a more bushy growth habit with greater vigor and forms red blossoms with a white eye. The 'Kormax' variety forms medium red single blossoms.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meizerbil'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during May while budded on *Rosa froebelli* understock and growing outdoors at Le Cannet des Maures, Var, France. Dimensions in centimeters are indicated at the bottom of the photograph together with comparative color information.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower-plan view-obverse;

FIG. 7—illustrates a specimen of an open flower-plan view-reverse;

FIG. 8—illustrates a specimen of a fully open flower-plan view-obverse;

FIG. 9—illustrates a specimen of a fully open flower-plan view-reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets-plan view-upper surface;

FIG. 15—illustrates a specimen of a leaf with five leaflets-plan view-under surface;

FIG. 16—illustrates a specimen of a leaf with seven leaflets-plan view-upper surface; and FIG. 17—illustrates a specimen of a cluster of buds.

DETAILED DESCRIPTION

The chart used in the identification of the colors is that of The Royal Horticultural Society (R.H.S. Colour Chart), London, England. Common color terms are to be accorded their customary dictionary significance. The description is based on the observation of one-year-old plants during May while budded on *Rosa froebelli* understock and growing outdoors at Le Cannet des Maures, Var, France.

Class: Floribunda.

Plant:

*Height.*—Approximately 80 cm on average at the end of the growing season.

*Width.*—Approximately 80 cm on average at the end of the growing season.

*Habit.*—Compact and bushy.

Branches:

*Color.*—Young stems: near Yellow-Green Group 146B. Adult wood: near Yellow-Green Group 144A.

*Thorns.*—On young stems: Small prickles: commonly absent. Long prickles: Configuration: upright and curved downward on the upper surface, slightly concave on the under surface, and narrow at the base. Quantity: approximately 5 on average on a stem length of 10 cm. Length: approximately 6 mm or more on average. Color: near Greyed-Red Group 181A. On adult stems: Small prickles: commonly absent. Long prickles: Configuration: upright and curved downward on the upper surface, slightly concave on the under surface, and narrow at the base. Quantity: approximately 3 on average on a stem length of 10 cm. Length: approximately 6 mm or more on average. Color: near Greyed-Orange Group 175A.

Leaves:

*Stipules.*—Adnate, pectinate and broad, approximately 1.4 cm in length on average, approximately 0.6 cm in width on average, near Green Group 137C on the upper surface, and near Yellow-Green Group 146B on the under surface.

*Petioles.*—Upper surface: near Yellow-Green Group 147B in coloration. Under surface: near Yellow-Green Group 146C in coloration. Length: approximately 2.1 cm for the terminal leaflet.

*Rachis.*—Upper surface: near Yellow-Green Group 147B in coloration. Under surface: near Green Group 137D in coloration.

*Leaflets.*—Number 3, 5 and 7 (most often). Shape: generally elliptic with an obtuse base and an acuminate tip. Size: the terminal leaflets commonly are approximately 3.4 cm in length on average and approximately 2 cm in width on average. Serration: small and single (as illustrated). Texture: physically firm and thick. General appearance: somewhat sparse and semi-glossy on the upper surface. Color (young foliage): Upper surface: near Green Group 137A. Under surface: near Green Group 137D. Color (adult foliage): Upper surface: near Green Group 137A. Under surface: near Yellow-Green Group 146B.

Inflorescence:

*Number of flowers.*—Pluriflorous per stem.

*Peduncle.*—Glandular, near Yellow-Green Group 146C, approximately 2 cm in length on average, and approximately 0.2 cm in diameter on average.

*Sepals.*—Upper surface: smooth and near Green Group 137D in coloration. Under surface: smooth and near Yellow-Green Group 146A in coloration. Configuration: approximately 1.7 cm in length on average, and approximately 0.6 cm in width on average at the widest point.

*Buds.*—Shape: conical. Size: small. Length: approximately 1 cm on average. Width: approximately 0.7 cm on average at the widest point. Color: Upper surface: near Red Group 53C as the calyx breaks. Under surface: near Red-Purple Group 57A as the calyx breaks.

*Flower.*—Shape: flat, cup-shaped. Diameter: approximately 4.5 cm on average. Color (in the course of opening): Upper surface: near Red-Purple Group 57A. Under surface: near Red-Purple Group 57B. Basal petal spot: yellow (as illustrated). Color (when fully open): Upper surface: near Red-Purple Group 57B. Under surface: near Red-Purple Group 57C. Basal petal spot: yellow (as illustrated). Fragrance: none. Lasting quality: the blossoms commonly last approximately 15 days on average when cut and placed in a vase. Petal number: commonly approximately 15 to 17 on average under normal growing conditions. Petal shape: rounded. Petal texture: consistent and somewhat firm. Petal arrangement: imbricated, and without petaloids. Petal drop: good with the petals commonly detaching cleanly before drying. Stamen number: approximately 116 on average. Anthers: regularly arranged around the styles, approximately 0.1 cm in size on average, and near Yellow-Orange Group 15A in coloration. Pollen: present. Filaments: approximately 0.3 cm in length on average and near Yellow Group 7B in coloration. Pistils: approximately 30 on average. Stigmas: approximately 0.2 cm in size on average and near Yellow Group 4D in coloration. Styles: approximately 0.4 cm in length on average, and near Yellow Group 2D in coloration. Receptacle: smooth, pitcher-shaped in longitudinal section, approximately 0.5 cm in length on average, approximately 0.3 cm in width on average at the widest point, and near Green Group 137D in coloration.

Development:

*Vegetation.*—Strong.

*Blooming.*—Medium season.

*Resistance to diseases.*—Good, particularly with respect to Oidium and Black Spot.

I claim:

1. A new and distinct Floribunda rose plant characterized by the following combination of characteristics:

(a) exhibits a compact bushy growth habit, (b) forms attractive red-purple blossoms having a yellow eye, (c) forms attractive dark green semi-glossy foliage, (d) displays excellent resistance to disease, and (e) is well suited for growing as ornamentation in parks and gardens;

substantially as herein shown and described.

* * * * *

METERBIL
CM